United States Patent [19]

Theiling

[11] Patent Number: 4,723,945
[45] Date of Patent: Feb. 9, 1988

[54] HYPODERMIC SYRINGE

[75] Inventor: Manfred Theiling, Bünde, Fed. Rep. of Germany

[73] Assignee: Bunder Glas GmbH, Bünde, Fed. Rep. of Germany

[21] Appl. No.: 879,414

[22] Filed: Jun. 27, 1986

Related U.S. Application Data

[63] Continuation-in-part of Ser. No. 635,699, Jul. 30, 1984, abandoned.

[30] Foreign Application Priority Data

May 3, 1984 [EP] European Pat. Off. ......... 84104961.2

[51] Int. Cl.$^4$ .............................................. A61M 5/18
[52] U.S. Cl. ..................................... 604/232; 604/242
[58] Field of Search ............... 604/232, 240, 241, 242, 604/234, 235, 283

[56] References Cited

U.S. PATENT DOCUMENTS

| | | | |
|---|---|---|---|
| 1,740,459 | 12/1929 | Hein | 604/242 |
| 1,818,670 | 8/1931 | Bixler | 604/234 |
| 2,755,801 | 7/1956 | Morando | 604/242 |
| 3,491,757 | 1/1970 | Arce | 604/242 |
| 3,556,099 | 1/1971 | Knight | 604/232 |
| 3,811,441 | 5/1974 | Sarnoff | 604/232 |
| 3,848,593 | 11/1974 | Baldwin | 604/232 |
| 3,895,633 | 7/1975 | Bartner et al. | 604/232 |
| 3,958,570 | 5/1976 | Vogelman et al. | 604/242 |
| 4,333,458 | 6/1982 | Margulies et al. | 604/232 |

FOREIGN PATENT DOCUMENTS 0166433 7/1953 Australia .............................. 604/242

Primary Examiner—Stephen C. Pellegrino
Attorney, Agent, or Firm—William A. Drucker

[57] ABSTRACT

A hypodermic syringe consists of a syringe body (3) and a cylindrical ampoule (4) inserted therein, a Luer-Lock connection for a cannula (1) being provided on the syringe body (3), the Luer-Lock connection being constructed in two pieces, the connecting member (10) being fixed to the cylindrical ampoule (4) and the threaded sleeve (8) being fixed to the syringe body (3), the connecting member (10) having an axial connecting passage (13) to the interior of the cylindrical ampoule (4), which can be sealed by a removable sealing plug (7), and the cylindrical ampoule (4) being positionally fixed at one end with a conical surface (14) engaged in a tapered bore (8b) in the sleeve (8), and being secured at the other end against axial displacement in the syringe body (3) by means of a retaining collar (5) which can be removably fixed to the syringe body (3) and which acts through a bearing ring (21) against the end (4b), the improved syringe, as a prefilled disposable syringe, ensuring with easy handling a secure and tight attachment of the cannula to the Luer-Lock connection as a result of the two-piece construction of the Luer-Lock connection and guaranteeing a connection free from perforation and fragmentation.

8 Claims, 8 Drawing Figures

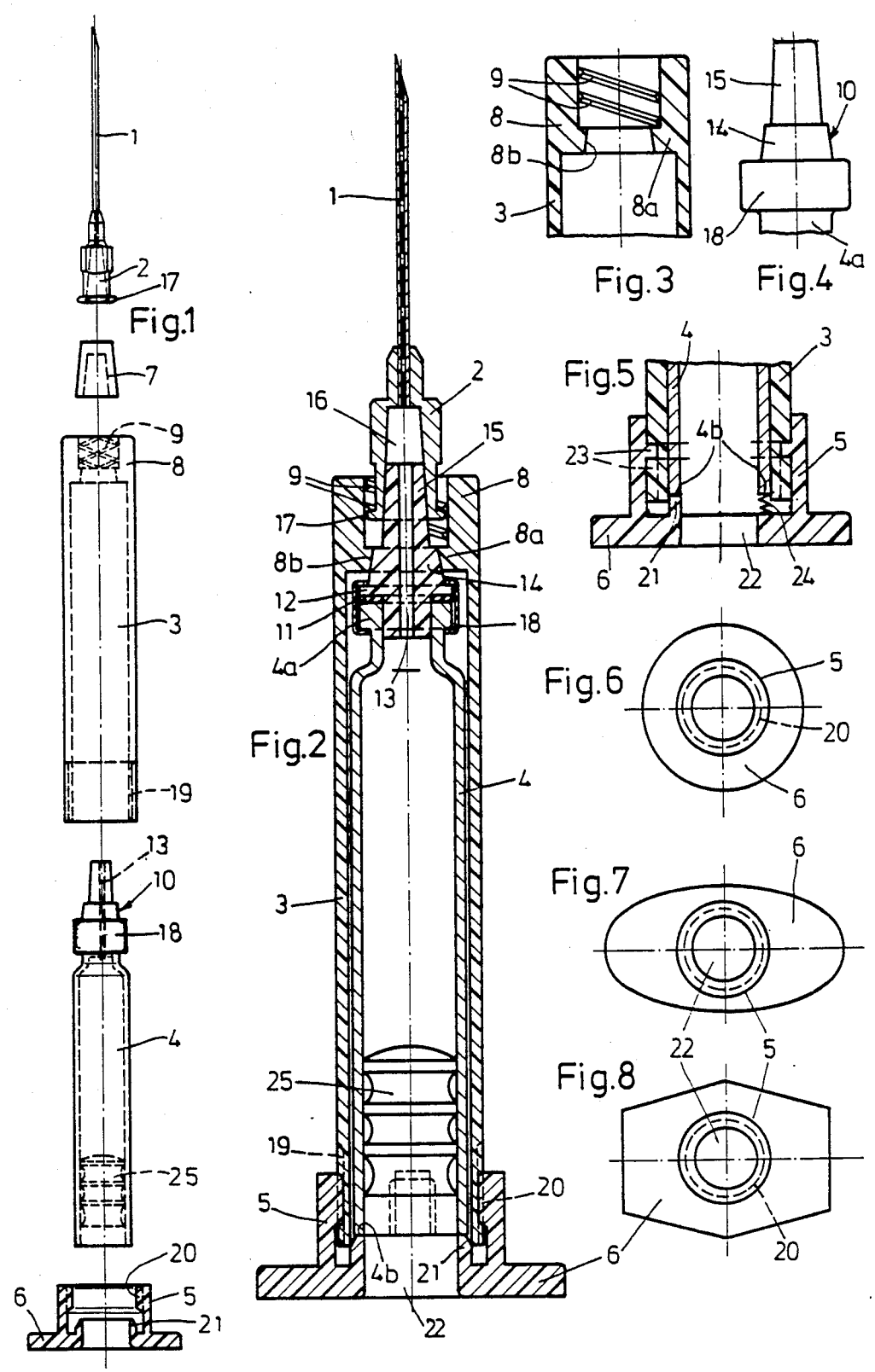

HYPODERMIC SYRINGE

This application is a continuation-in-part of Ser. No. 06/635/699 filed July 30, 1984 and now abandoned.

BACKGROUND OF THE INVENTION

The invention relates to a hypodermic syringe, consisting of a syringe body and a cylindrical ampoule inserted therein, which is provided with a Luer-Lock connection for a cannula, the threaded part of the connection being at one end of the syringe body.

In such known hypodermic syringes to be found on the market the Luer-Lock connection with its socket-like internal thread is sometimes fitted with a subsequently installed cone. This Luer-Lock design does not guarantee secure connection between the cannula and the Luer-Lock cone by means of the cannula-side connecting piece which interacts with the threaded section because, when screwing the connecting piece into the thread, the cone can be displaced to one side and, as a result, a firm and tight connection between the cone and the connecting piece of the cannula is no longer possible, so that the contents of the ampoule can escape between these two parts.

Furthermore, the cone of the Luer-Lock connection mounted on the syringe body is provided with a transfer cannula, by means of which a diaphragm seal of the cylindrical ampoule is penetrated when pushing the former in the direction of the cone, as a result of which a passage from the interior of the ampoule to the cannula is produced. As a consequence of this penetration of the diaphragm seal, minute particles of the diaphragm are often broken away, so that an unfragmented connection between cannula and cylindrical ampoule cannot take place.

OBJECT OF THE INVENTION

It is the object of the invention to provide an improved hypodermic syringe, with a Luer-Lock connection, with which it is possible to make a tight and strong connection between the cannula and the Luer-Lock cone, free from perforation and consequently fragmentation, and which is simple and safe to handle as a pre-filled disposable syringe.

SUMMARY OF THE INVENTION

In accordance with the invention, a hypodermic syringe comprises:

(i) a tubular syringe body having a first open longitudinal end and a second open longitudinal end, said body having adjacent its first longitudinal end a transverse wall with a conical bore, said body having an internal thread between said transverse wall and said first open end;

(ii) a cylindrical ampoule disposed in said syringe body and having a first longitudinal end and a second longitudinal end, said ampoule having a piston slidable within it;

(iii) a connecting means projecting axially at said first end of the ampoule and having a first conical surface and a coaxial second conical surface of lesser cross-section than said first conical surface extending from the end of said first conical surface, said connecting means including a passage through it, said connecting means having its first conical surface seated into said conical bore of said syringe body;

(iv) a retaining member axially adjustable on said second open end of the syringe body and including presser means bearing against the second end of the ampoule such that the ampoule is firmly held, against longitudinal movement relative to the syringe body, between said transverse wall and said retaining member, (v) a coupling member carrying a cannula, said coupling member having an internal chamber communicating with said cannula, said internal chamber being bounded by an internal conical surface engaged over said second conical surface of the connecting means, said coupling member extending into said syringe body at the first longitudinal open end thereof and coacting with said internal thread, such that by rotation of said coupling member with respect to said syringe body the internal conical surface of the coupling member may be firmly engaged in fluid-tight manner on the second conical surface of the connecting means.

The presser means may be a bearing ring, and may include a compression spring.

The retaining member may include a finger rest, and said finger rest may serve as the presser means bearing against the second end of the ampoule.

In a first form, the connecting means is formed integrally on the first end of the ampoule. In another form, the connecting means is a connecting member secured on the first end of the ampoule.

Advantageously, the second coaxial conical surface of the connecting means projects axially beyond the first end of the syringe body.

The retaining means may be a collar with a finger-rest and may be fixed by means of screwing, bayonet fitting, or locking connection to act against the end of the filled cylindrical ampoule inserted into the syringe body, to fix the former in the axial direction.

By this means it is achieved that both the length tolerance of the cylindrical ampoule is accommodated and furthermore that in each case the first conical surface on the cylindrical ampoule is pressed firmly into the conical bore of the transverse wall of the syringe body and is positionally fixed.

In the hypodermic syringe according to the invention the Luer-Lock connection is constructed in two parts, the cone being provided on the cylindrical ampoule, and the threaded section being provided on the syringe body. The filled cylindrical ampoule is held in the syringe body, positionally secured in the axial direction. When the syringe is used, the coupling member for the cannula can be mounted by its internal conical sealing surface on the second conical surface of the connecting means and is then screwed into the thread of the syringe body, as a result of which the coupling member draws the conical surfaces firmly into a very tight and strong connection.

The connecting means of the cylindrical ampoule is provided with an axial connecting passage, and this can be sealed by means of a removable sealing plug.

When the cannula is to be attached, this sealing plug is firstly removed and then a communication between the cylindrical ampoule interior and the cannula is immediately established, so that no sealing section of the cylindrical ampoule has to be penetrated and, as a result, a connection without perforation and fragmentation takes place between the cannula and the cylindrical ampoule.

The filled cylindrical ampoule, sealed with the sealing plug, is held securely in position in the syringe body, and, by means of the Luer-Lock connection, can be connected with the cannula easily and safely, as well as very tightly.

BRIEF DESCRIPTION OF THE DRAWINGS

An embodiment according to the invention is described in greater detail below with reference to the accompanying drawing.

In the drawing:

FIG. 1 is a side elevation, seen partly in section and in separated condition, of a hypodermic syringe consisting of a cannula with coupling member, syringe body with Luer-Lock thread, a cylindrical ampoule with Luer cone, a retaining collar with finger-rest, and a removable sealing plug which can be mounted on a conical surface of the cylindrical ampoule;

FIG. 2 is a longitudinal section through the assembled hypodermic syringe;

FIG. 3 is a longitudinal section through the threaded region of the Luer-Lock connection on the syringe body;

FIG. 4 is a side elevation of a connecting member on the cylindrical ampoule;

FIG. 5 is a longitudinal section through the retaining collar with finger-rest, and with a bearing ring or compression spring, held on the syringe body by means of a bayonet fitting;

FIGS. 6 to 8 are plan views of the retaining collar with difference finger-rests.

DESCRIPTION OF THE PREFERRED EMBODIMENTS

The hypodermic syringe according to the invention is intended for use as a disposable syringe and consists of a cannula 1 with coupling member 2, a syringe body 3, a filled cylindrical ampoule 4 and a retaining collar 5 with finger-rest 6, as well as a sealing plug 7 for the filled cylindrical ampoule 4.

The syringe body 3 and the cylindrical ampoule 4 together form a two-piece Luer-Lock connection for the cannula 1, which by means of its coupling member 2 can be connected releasably, but tightly and securely, with both the cylindrical ampoule 4 as well as with the syringe body 3.

The syringe body 3 is made from a cylindrical plastic tube of circular cross-section, preferably of transparent plastic, and has at one end a section of a Luer-Lock connection, namely the threaded section, which consists of a sleeve 8 with an internal thread 9. This threaded sleeve 8 is part of the tubular syringe body 3, but has a greater wall thickness compared to the rest of the syringe body wall.

The threaded sleeve 8 has a transverse wall 8a with a conical bore 8b.

The cylindrical ampoule 4 is accommodated in the syringe body 3 and at one end is fitted with the second part of the Luer-Lock connection, namely the connecting member 10. One part 8,9 of the Luer-Lock connection is provided on the syringe body 3 and the second part (member 10) on the cylindrical ampoule 4. This connecting member 10 is engaged on one end of the ampoule 4 and rests by its flange 12 on the end face of the ampoule neck 4a with a ring seal 11 interposed. The member 10 is firmly connected to the cylindrical ampoule 4 by means of a flanged cap 18 which grips the flange 12 and the ampoule neck 4a.

The connecting member 10 has an axial passage 13 in communication with the interior of the cylindrical ampoule 4, so that the latter is connected with the cannula 1 through the coupling member 2 for the flow of the contents out of the cylindrical ampoule 4.

The connecting member 10 has a first conical surface 14 which engages into the conical bore 8b so that the cylindrical ampoule 4 is firmly centered an held against longitudinal movement in the direction of the cannula 1.

The member 10 has a second coaxial conical surface 15, of lesser cross-section compared to the first conical surface 14, and extending from the end thereof. Said conical surface 15 projects beyond the end face of the syringe body 3 by a certain amount when the cylindrical ampoule 4 is inserted (cf. FIG. 2).

The coupling member 2, firmly connected to the cannula 1, has an internal chamber bounded by an internal conical surface 16 engaging onto the conical surface 15, and this coupling member 2 engages by part of its length into the sleeve 8 and has a flange 17 projecting outwards which interacts with the thread 9.

The end of the cylindrical ampoule 4 remote from the connecting member 10 contains a sealing plunger 25 which can be moved by means of a piston, which is not shown, for forcing out the contents of the ampoule, preferably a liquid or a paste.

The cylindrical ampoule 4 is rigidly positioned in the syringe body 3 at one end by its connecting member engaging in the conical bore 8b, and is held at its other end against axial displacement in the syringe body 3, by means of the retaining collar 5 with finger-rest 6, which can be connected to the syringe body 3 by threading, or by bayonet fitting, or by locking connection or similar device, so that the inserted cylindrical ampoule 4 is positionally fixed in the syringe body 3.

As seen in FIGS. 1 and 2, the second end of the syringe body 3, remote from the sleeve 8, is provided with a male thread 19, onto which the retaining collar 5 having a female thread is screwed. The retaining collar 5 has inside it a bearing ring 21 acting on the free end 4b of the cylindrical ampoule 4, preferably a compression ring, by means of which the cylindrical ampoule 4 is pressed with its conical surface 14 firmly against the conical bore 8b.

The retaining collar 5 includes a passage 22 passing through the bearing ring 21 for the piston which can be connected to the plunger 25 by means of a screwed connection.

According to the embodiment in FIG. 5, the retaining collar 5 is releasably connected to the syringe body 3 by means of a bayonet fitting 23, the interacting grooves and projections of which are provided respectively internally on the retaining collar 5 and externally on the syringe body 3, as a result of which the retaining collar 5, similarly provided with a bearing ring 21 can act directly on the end 4b of the ampoule (cf. left-hand half of FIG. 5).

There is furthermore the option of fixing the retaining collar 5 to the syringe body 3 by means of a locking connection (groove and ribbing connection) the interacting locking elements being similarly provided on the inside of the retaining collar 5, and on the outside of the syringe body 3.

With the various modes of attaching the retaining collar 5, a compression spring 24 can be inserted between the bearing ring 21 of the retaining collar 5 and the end 4b of the ampoule, (cf. right-hand half of FIG. 5).

The finger-rest 6 can have various shapes, such as circular (FIG. 6), oval (FIG. 7), or multi-sided (FIG. 8). The finger-rest is advantageously made of plastic material in one piece with the retaining collar 5 and the bearing ring 21.

The connecting member 10 is preferably made of plastic material in one piece, and the coupling member 2 with the cannula 1 may consist of metal, or of plastic material.

There is inserted, into the syringe body 3, at the factory, the filled cylindrical ampoule 4 which has a small play between its casing wall and the casing wall of the syringe body 3, and which is engaged firmly by its connecting member with its conical surface 14 centered in the conical bore 8b. The retaining collar is then screwed on to the other end of the syringe body 3 (or attached by bayonet fitting or locking connection), as a result of which the bearing ring 21 presses against the end 4b, and the cylindrical ampoule 4 is thus held fast.

The second conical surface 15 of the connecting member 10 projects out of the sleeve 8 of the syringe body 3 in the axial direction, and its axial passage 13 is temporarily sealed by means of a removable sealing plug 7. The syringe body, thus supplemented, is then sterilely packed with the cannula 1.

When using the syringe, the user removes the sealing plug 7 and mounts the cannula 1 by its coupling member 2 on the conical surface 15. The user then rotates the coupling member 2, so that flange 17 thereof interacts with the thread 9 and the conical surface 15 is drawn firmly into the internal conical seal 16, so that a fluid-tight connection is obtained between the two parts. With this Luer-Lock connection, the cylindrical ampoule 4 cannot move in the syringe body 3, as a result of its being clamped at both ends in the syringe body 3, and by this means a tight and very strong connection of the cannula 1 to the connecting member is achieved.

Simultaneously with the mounting of the cannula 1, a connection of the interior of the cylindrical ampoule 4 with the cannula 1 is produced through the axial passage 13, without a sealing element or the like having to be penetrated.

Also within the scope of the invention is the use of the plate-like finger-rest 6 itself acting in place of the bearing ring 21, so that no projecting ring 21 need be provided. However, the cylindrical ampoule 4 would have to project by its end 4b out of the syringe body 3 to some degree.

In a modification, not illustrated, the connecting member 10, with its first conical surface 14 and its second conical surface 15, are formed integrally in one piece with the adjacent end of the cylindrical ampoule 4, thereby eliminating any need for the flange 12, ring seal 11, and flanged cap 18.

I claim:

1. A hypodermic syringe comprising:
   (i) a tubular syringe body having a first open longitudinal end and a second open longitudinal end, said body having adjacent its first longitudinal end a transverse wall with a conical bore, said body having an internal thread between said transverse wall and said first open end,
   (ii) a cylindrical ampoule disposed in said syringe body and having a first longitudinal end and a second longitudinal end, said ampoule having a piston slidable within it,
   (iii) a connecting means projecting axially at said first end of the ampoule and having a first conical surface and a coaxial second conical surface of lesser cross-section than said first conical surface extending from the end of said first conical surface, said connecting means including a passage through it, said connecting means having its first conical surface seated into said conical bore of said syringe body,
   (iv) a retaining member axially adjustable on said second open end of the syringe body and including presser means bearing against the second end of the ampoule such that the ampoule is firmly held, against longitudinal movement relative to the syringe body, between said transverse wall and said retaining member, and
   (v) a coupling member carrying a cannula, said coupling member having an internal chamber communicating with said cannula, said internal chamber being bounded by an internal conical surface engaged over said second conical surface of the connecting means, said coupling member extending into said syringe body at the first longitudinal open end thereof and coacting with said internal thread, such that by rotation of said coupling member with respect to said syringe body the internal conical surface of the coupling member may be firmly engaged in fluidtight manner on the second conical surface of the connecting means.

2. A hypodermic syringe, as claimed in claim 1, wherein said presser means is a bearing ring.

3. A hypodermic syringe, as claimed in claim 1, wherein said presser means includes a compression spring.

4. A hypodermic syringe, as claimed in claim 1, wherein said retaining member includes a finger-rest.

5. A hypodermic syringe, as claimed in claim 4, wherein said finger-rest serves as said presser means bearing against the second end of the ampoule.

6. A hypodermic syringe, as claimed in claim 1 wherein said connecting means is formed integrally on said first end of said ampoule.

7. A hypodermic syringe, as claimed in claim 1, wherein said connecting means is a connecting member secured on said first end of said ampoule.

8. A hypodermic syringe, as claimed in claim 1, wherein said second coaxial conical surface of said connecting means projects axially beyond said first end of said syringe body.

* * * * *